(12) United States Patent
Suzuki et al.

(10) Patent No.: US 7,722,587 B2
(45) Date of Patent: May 25, 2010

(54) DISPOSABLE DIAPER

(75) Inventors: Sachiyo Suzuki, Kagawa-ken (JP); Toshifumi Otsubo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 296 days.

(21) Appl. No.: 10/917,318

(22) Filed: Aug. 13, 2004

(65) Prior Publication Data
US 2005/0038401 A1 Feb. 17, 2005

(30) Foreign Application Priority Data
Aug. 14, 2003 (JP) ............... 2003-207554

(51) Int. Cl.
*A61F 13/15* (2006.01)
(52) U.S. Cl. ............ 604/385.101; 604/385.08; 604/385.01
(58) Field of Classification Search ............ 604/385.19, 604/385.16, 385.02, 385.01, 385.101, 385.17, 604/385.08, 385.26
See application file for complete search history.

(56) References Cited

U.S. PATENT DOCUMENTS

| | | | |
|---|---|---|---|
| 3,848,599 A | 11/1974 | Schaar | |
| 4,573,990 A | 3/1986 | Ohsaki | |
| 4,695,278 A | 9/1987 | Lawson | |
| 4,892,536 A | 1/1990 | DesMarais et al. | |
| 4,909,803 A | 3/1990 | Aziz et al. | |
| 4,990,147 A | 2/1991 | Freeland | |
| 5,171,236 A | 12/1992 | Dreier et al. | |
| 5,306,266 A | 4/1994 | Freeland | |
| 5,342,342 A | 8/1994 | Kitaoka | |
| 5,514,121 A | 5/1996 | Roe et al. | |
| 5,527,300 A | 6/1996 | Sauer | |
| 5,558,661 A | 9/1996 | Roe et al. | |
| 5,576,091 A | 11/1996 | Zajaczkowski et al. | |
| 5,601,544 A * | 2/1997 | Glaug et al. ............ | 604/385.28 |
| 5,779,690 A | 7/1998 | Gustafsson et al. | |
| 5,810,799 A | 9/1998 | Slater | |
| 5,817,086 A | 10/1998 | Kling | |
| 5,853,403 A | 12/1998 | Tanzer et al. | |

(Continued)

FOREIGN PATENT DOCUMENTS

EP 0 908 162 4/1999

(Continued)

OTHER PUBLICATIONS

European Search Report for 05745617 issued Nov. 14, 2007.

(Continued)

*Primary Examiner*—Tatyana Zalukaeva
*Assistant Examiner*—Lynne Anderson
(74) *Attorney, Agent, or Firm*—Lowe Hauptman Ham & Berner LLP

(57) ABSTRACT

A disposable diaper has a chassis and a body fluid absorbent structure. The body fluid absorbent structure comprises a panel of body fluid absorbent material and a liquid-pervious sheet covering a surface of the panel facing the wearer's skin. The diaper is provided with a plurality of crossover members extending across the body fluid absorbent structure and facing the liquid-pervious sheet. The crossover member has its transversely opposite end portions bonded to the diaper in the vicinity of the side edge portions of the body fluid absorbent structure and its intermediate portion defined between the side end portions not bonded to the liquid-pervious sheet.

4 Claims, 10 Drawing Sheets

U.S. PATENT DOCUMENTS

| | | | |
|---|---|---|---|
| 6,010,490 | A | 1/2000 | Freeland et al. |
| 6,123,692 | A | 9/2000 | Guidotti et al. |
| 6,152,907 | A | 11/2000 | Widlund et al. |
| 6,168,584 | B1 | 1/2001 | Allen et al. |
| 6,179,820 | B1 | 1/2001 | Fernfors |
| 6,248,098 | B1 | 6/2001 | Sayama |
| 6,464,676 | B2 | 10/2002 | Mishima |
| 6,471,682 | B2* | 10/2002 | Kashiwagi ............ 604/385.27 |
| 6,506,185 | B1* | 1/2003 | Sauer et al. ........... 604/385.01 |
| 6,527,756 | B1 | 3/2003 | Mishima et al. |
| 6,692,475 | B2* | 2/2004 | Mishima ................ 604/385.19 |
| 6,699,228 | B1* | 3/2004 | Chmielewski et al. . 604/385.28 |
| 6,786,895 | B1 | 9/2004 | Schmitz |
| 6,869,423 | B2 | 3/2005 | Onishi et al. |
| 6,921,394 | B2 | 7/2005 | Sayama et al. |
| 7,204,830 | B2 | 4/2007 | Mishima et al. |
| 2002/0013567 | A1 | 1/2002 | Mishima et al. |
| 2002/0069714 | A1 | 6/2002 | Allner et al. |
| 2002/0077615 | A1 | 6/2002 | Mishima |
| 2002/0099351 | A1 | 7/2002 | Onishi et al. |
| 2002/0120248 | A1 | 8/2002 | Onishi et al. |
| 2002/0151861 | A1* | 10/2002 | Klemp et al. ......... 604/385.19 |
| 2004/0122404 | A1* | 6/2004 | Meyer et al. .......... 604/385.19 |
| 2005/0228357 | A1 | 10/2005 | Mishima et al. |
| 2005/0228358 | A1 | 10/2005 | Mishima et al. |
| 2006/0009746 | A1 | 1/2006 | Nakajima et al. |
| 2006/0135931 | A1 | 6/2006 | Suzuki et al. |

FOREIGN PATENT DOCUMENTS

| | | |
|---|---|---|
| EP | 0998891 A2 | 5/2000 |
| EP | 1057463 A2 | 12/2000 |
| EP | 1059073 A2 | 12/2000 |
| EP | 1 064 899 A1 | 1/2001 |
| EP | 1064899 A1 | 1/2001 |
| EP | 1084688 A2 | 3/2001 |
| GB | 2294398 A | 5/1996 |
| JP | 5-285174 | 11/1993 |
| JP | 11-318976 | 11/1999 |
| JP | 11-342156 | 12/1999 |
| JP | 2000-126227 A | 5/2000 |
| WO | 94/14395 A1 | 7/1994 |
| WO | 00/28929 A1 | 5/2000 |

OTHER PUBLICATIONS

European Search Report of Application No. 04771669.1—2124 / 1661536 PCT/JP2004011702 mailed May 6, 2009.

* cited by examiner

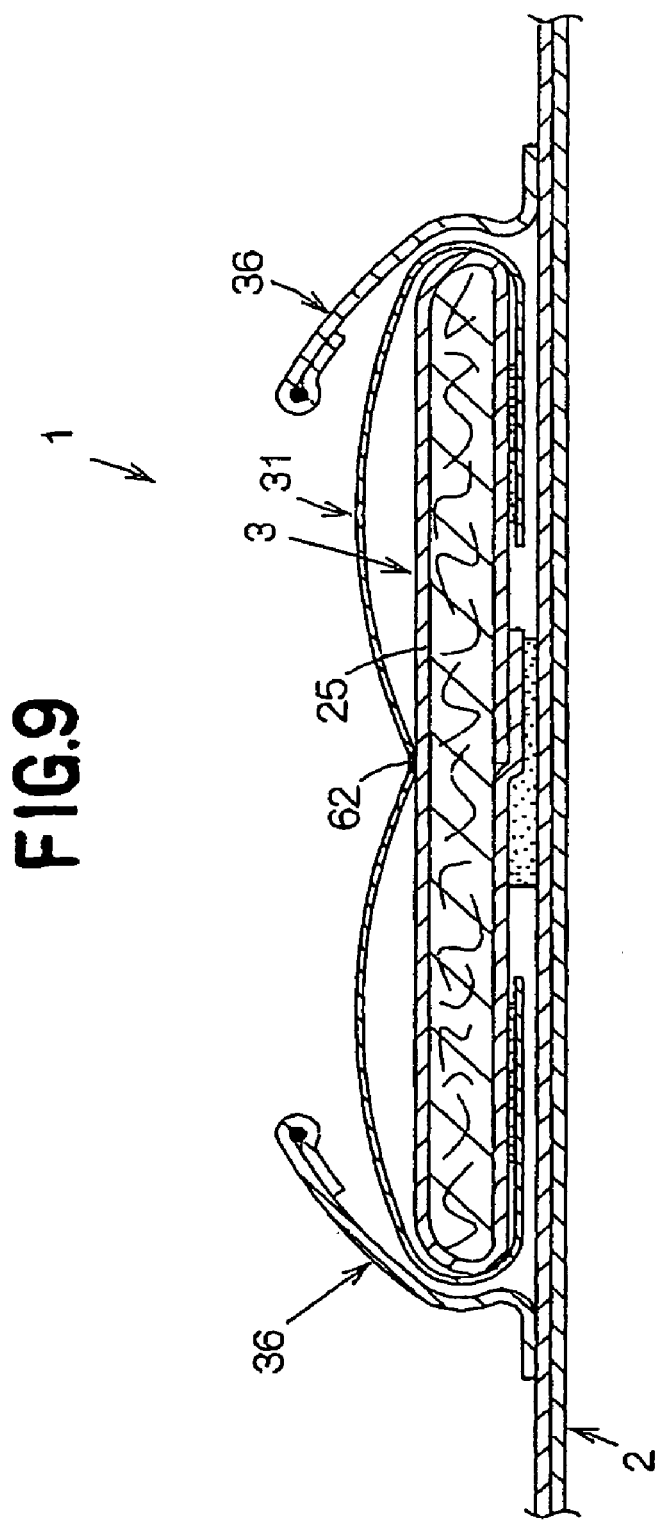

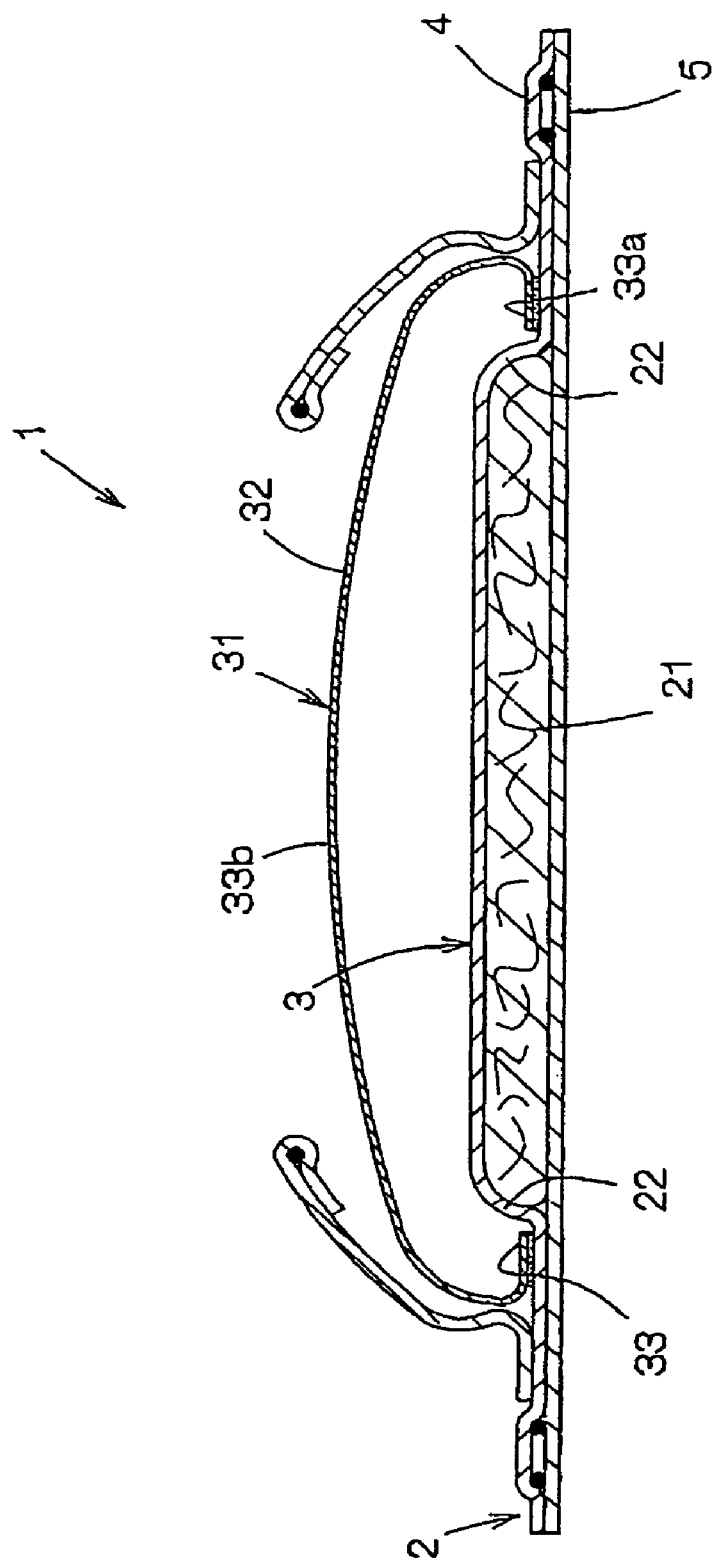

DISPOSABLE DIAPER

RELATED APPLICATIONS

The present application is based on, and claims priority from, Japanese Application Serial Number 2003-207554, filed Aug. 14, 2003, the disclosure of which is hereby incorporated by reference herein in its entirety.

BACKGROUND OF THE INVENTION

The present invention relates to a disposable diaper for absorption and containment of body wastes.

A disposable diaper disclosed in Japanese Unexamined Patent Application Publication No. 1999-342156 (hereinafter referred to as "Citation 1") includes an upper sheet above a liquid-pervious topsheet. The upper sheet is bonded to the diaper along an outer peripheral portion of the upper sheet and a crotch region of the diaper is formed in its transversely middle zone with an opening which is, in turn, provided along its peripheral portion with an elastic member attached in stretched state thereto. The elastic member contracts and the peripheral portion of the opening is spaced apart from the topsheet as the diaper is curved in a back-and-forth direction. This known diaper allows body wastes to be caught in a space defined between the upper sheet and the topsheet by aligning the opening of the upper sheet with the wearer's anus and urinary organs. Such upper sheet serves as means adapted to prevent body wastes from coming in contact with the wearer's skin. Thin rubber threads or the like are used as the elastic member attached to the upper sheet.

A disposable diaper disclosed in Japanese Unexamined Patent Application Publication No. 1993-285174 (hereinafter referred to as "Citation 2") includes an upper sheet a liquid-pervious first upper sheet and a liquid-resistant second upper sheet on the upper surface of the first upper sheet wherein the second upper sheet is formed in its middle zone with an opening extending in a back-and-forth direction of the diaper. Liquid-resistant flaps extending from transversely opposite side edges of the opening and these flaps are provided along respective outer side edge portions with elastic members. Longitudinally opposite end portions of each of the flaps are bonded to the second upper sheet. In this diaper also, the second upper sheet serves as a means adapted to prevent body wastes from coming in contact with the wearer's skin and thin rubber threads or the like are used as the elastic members attached to the second upper sheet.

Each of the diapers disclosed in Citations 1 and 2 includes the upper sheet provided above the topsheet covering the absorbent core and serving as a means to prevent body waste from coming in contact with the wearer's skin. In both cases, contraction of the elastic members attached to the upper sheet brings the upper sheet in close contact with the wearer's skin In these diapers, however, the elastic members comprising thin rubber threads may locally irritate the wearer's skin and cause pain and/or rash

SUMMARY OF THE INVENTION

In view of the problem as has been described above, it is an object of the present invention to improve the disposable diaper including a means to prevent body wastes from coming in contact with the wearer's skin so that such preventive means does not irritate the wearer's skin and/or does not cause rash or the like of the wearer's skin.

The object set forth above is achieved, according to the present invention, by a disposable diaper comprising: a chassis; a body fluid absorbent structure; the chassis having a back-and-forth direction, a width direction orthogonal to the back-and-forth direction, a front waist region, a rear waist region and a crotch region extending between the front and rear waist regions; the absorbent structure comprising a:body fluid absorbent panel lying on a side of the inner surface so as to extend on at least the crotch region of the front and rear waist regions and the crotch region and a liquid-pervious sheet covering a surface of the absorbent panel facing a wearer's skin.

The improvement according to the present invention is in that the absorbent structure is dimensioned in the crotch region to be narrower than the crotch region and has a pair of side edge portions extending in parallel to each other in the back-and-forth direction and, on the side facing the wearer's skin, the liquid-pervious sheet covering the absorbent panel is opposed to at least one crossover member extending across the absorbent structure above the absorbent structure in the width direction and having a width in a range of 5 to 250 mm as measured in the back-and-forth direction; and the transversely opposite end portions of the crossover member is bonded to the diaper in a vicinity of the transversely opposite side edge portions and the intermediate portion defined between the transversely opposite end portions is not bonded to the diaper whereby the intermediate portion is deformable so as to become convex from the outer surface to the inner surface as the chassis and the absorbent structure are deformed in the crotch region so as to become convex from the inner surface toward the outer surface and to reduce respective widths of these chassis and panel.

The present invention may include the following preferred embodiments:

The diaper has a plurality of the crossover members, a pair of the crossover members being-adjacent to each other in the back-and-forth direction located in a vicinity of the wearer's anus are spaced apart from each other by a dimension in a range of 10 to 150 mm in the back-and-forth direction so that feces discharged by the wearer pass through a clearance defined between these adjacent crossover members.

The crossover member is formed from a belt-like sheet made of a material selected from the group consisting of a nonwoven fabric containing thermoplastic synthetic fibers, a woven fabric containing thermoplastic synthetic fibers and a thermoplastic synthetic resin film.

The belt-like sheet is formed with a plurality of slits extending in the width direction of the diaper between transversely opposite end portions bonded to the diaper and each pair of the slits being adjacent to each other in the back-and-forth direction are spaced apart from each other by a dimension in a range of 2 to 80 mm.

The crossover member has a bending resistance in a range of 10 to 150 in the width direction of the diaper as measured using a sample having a width of 25 mm and a length of 150 mm and attached to the diaper in a state curved so as to become convex from the outer surface toward the inner surface.

The crossover member is attached to the diaper in a state curved so as to describe a C-shape.

The crossover member is attached to the diaper in a state curved so as to describe an Ω-shape.

The crossover member contains thermoplastic synthetic resin and is previously thermoformed so as to become convex from the outer surface toward the inner surface The diaper is provided with a pair of leak-barrier cuffs extending in the back-and-forth direction along the transversely opposite side edges of the body fluid absorbent panel and adapted to be elastically stretchable and contractible in the back-and-forth direction and the crossover member is provided inside the pair of the leak-barrier cuffs.

BRIEF DESCRIPTION OF THE DRAWINGS

FIG. 9 is a sectional view taken along the line IX-IX in FIG. 8; and

FIG. 10 is a view similar to FIG. 3, showing a further additional preferred embodiment of the invention.

DETAILED DESCRIPTION OF THE PREFERRED EMBODIMENTS

Details of a disposable diaper according to the present invention will be more fully understood from the description given hereunder with reference to the accompanying drawings.

Figure 1:
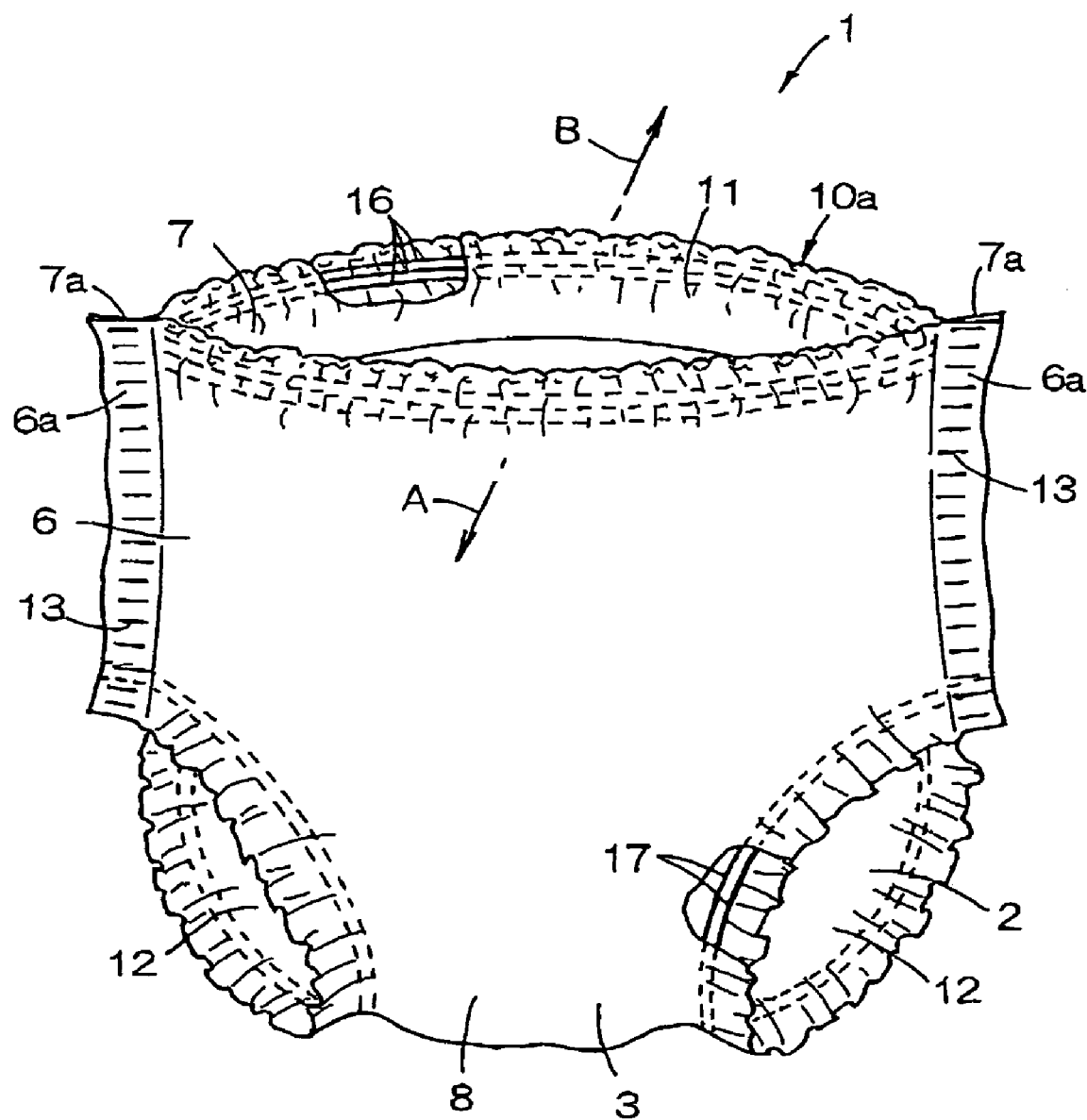
FIG. 1 is a partially cutaway perspective view showing a disposable diaper according to one embodiment of the invention.

FIG. 1 is a partially cutaway perspective view showing a disposable diaper 1 according to one embodiment of the invention. The diaper 1 comprises a pant-shaped chassis 2 and a body fluid absorbent structure 3 (See FIG. 2) having a generally rectangular planar shape. The chassis 2 comprises an inner sheet 4 facing the wearer's skin and an outer sheet 5 facing the wearer's garment, defining a front waist region 6, a rear waist region 7 and a crotch region 8 extending between the front and rear waist regions 6, 7. The front and rear waist regions 6, 7 respectively have transversely opposite marginal portions 6a, 7a overlapped and bonded together at a plurality of spots 13 arranged intermittently in the vertical direction as viewed in FIG. 1. The diaper 1 has a waist-hole 11 and a pair of leg-holes 12. Peripheral edge portion of the waist-hole 11 is provided with a plurality of waist-surrounding elastic members 16 interposed between the inner and outer sheets 4, 5 and bonded in a stretched state to the inner surface of at least one of these sheets 4, 5. Similarly, peripheral edge portions of the respective leg-holes 12 are provided with a plurality of leg-surrounding elastic members 17 interposed between these inner and outer sheets 4, 5 and bonded in a stretched state to the inner surface of at least one of these sheets 4, 5.

Figure 2:
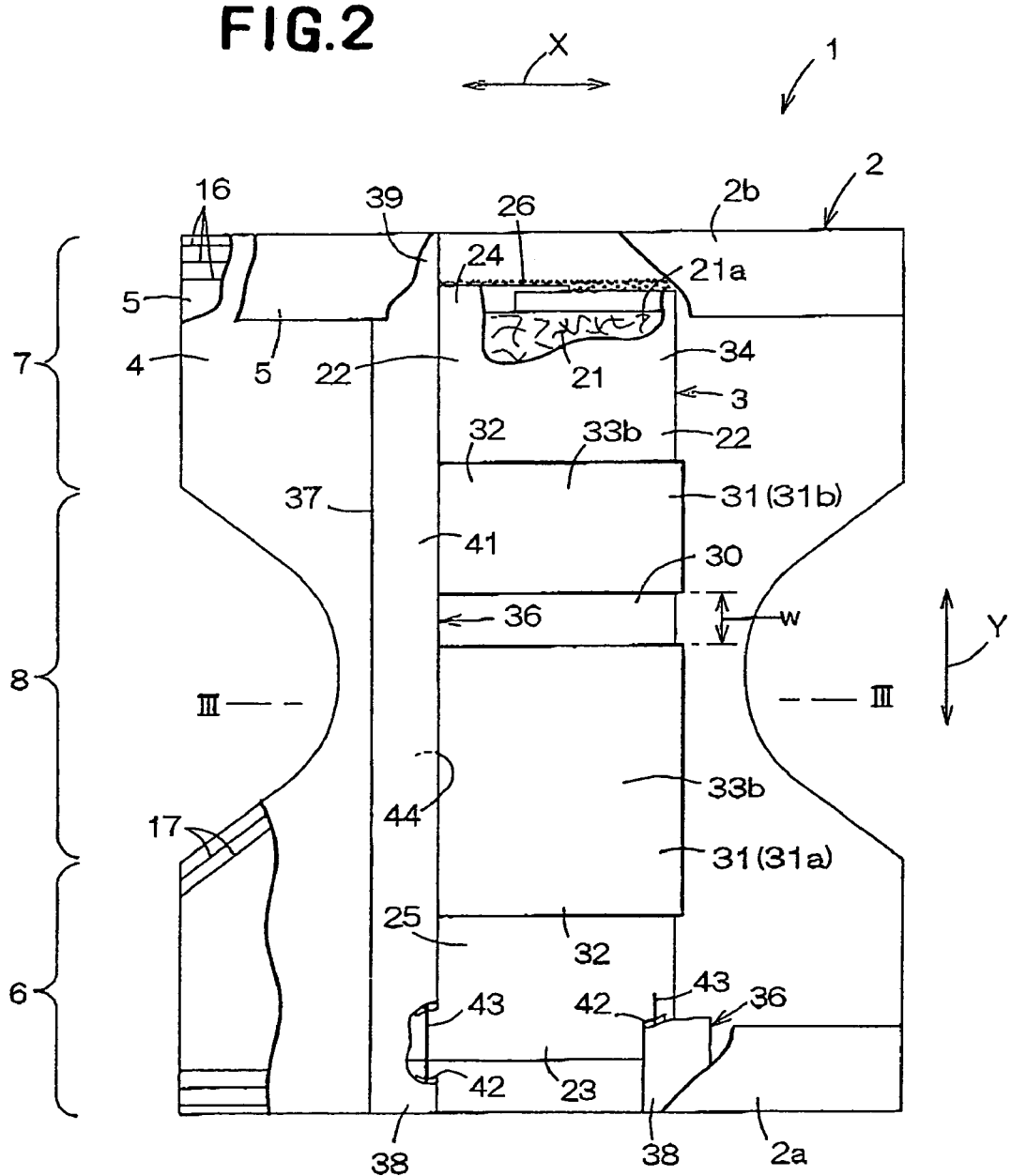
FIG. 2 is a partially cutaway plan view showing the disposable diaper peeled off and developed in a back-and-forth direction.
Figure 3:
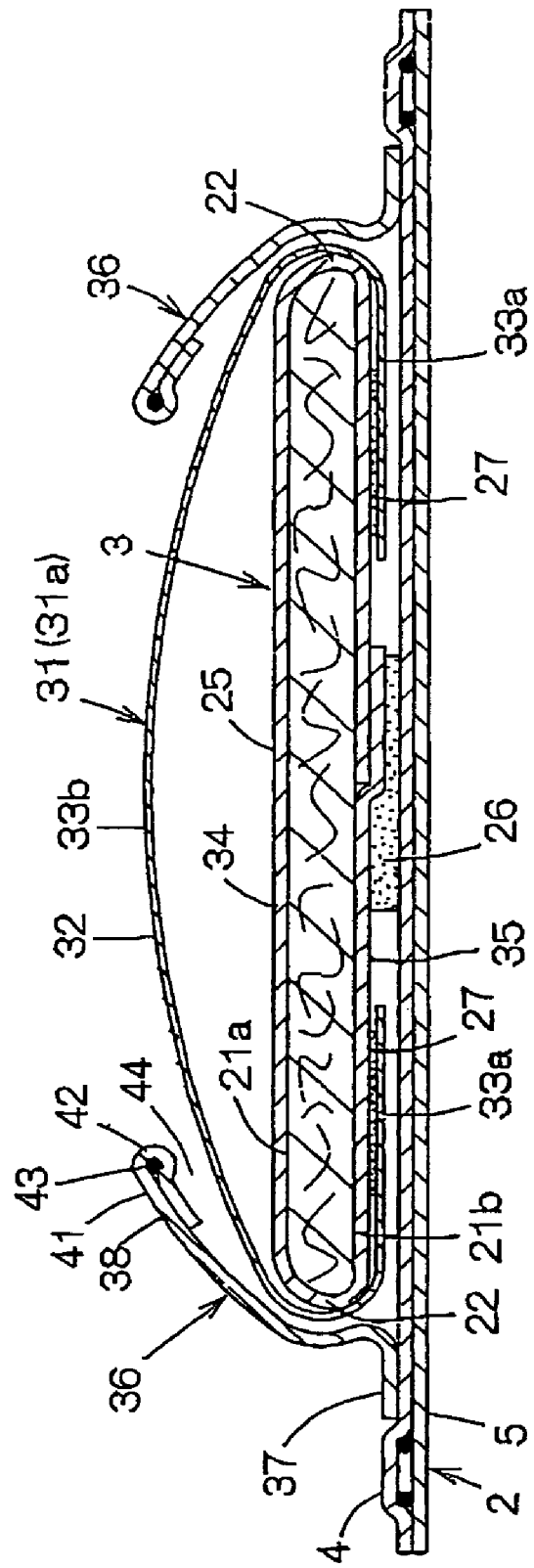
FIG. 3 is a sectional view taken along the line III-III in FIG. 2.

FIG. 2 is a partially cutaway plan view showing the disposable diaper 1 having front and rear waist region peeled off from each other at spots 13 and developed in directions indicated by arrows A and B and FIG. 3 is a sectional view taken along the line III-III in this plan view. The diaper 1 has a width direction indicated by a double-headed arrow X and a back-and-forth direction indicated by a double-headed arrow Y. The inner surface of the chassis 2 having a generally hourglass-like planar shape is provided in its middle zone as viewed in the width direction X with the body fluid absorbent structure 3. The body fluid absorbent structure 3 has its width smaller than the chassis 2 in the crotch region 8 and extends beyond the crotch region 8 in the back-and-forth direction Y. Along front and rear end portions 2a, 2b of the chassis 2, the outer sheet 5 is folded back onto the inner side of the diaper 1 and placed upon the inner sheet 4. The body fluid absorbent structure 3 comprises a panel of absorbent material 21 and a liquid-pervious cover sheet 25. The panel 21 is placed in the crotch region 8 and preferably extends beyond the crotch region 8 in the back-and-forth direction Y. The panel 21 has inner and outer surfaces 21a, 21b and at least the inner surface 21a is covered with the cover sheet 25 while the outer surface 21b of the panel 21 is also covered with the cover sheet 25 in the illustrated embodiment. The body fluid absorbent structure 3 constructed in the manner has inner and outer surfaces 34, 35, a pair of transversely opposite side edge portions 22 extending in the back-and-forth direction Y and front and rear end portions 23, 24 extending in the width direction X. The outer surface 35 has an intermediate zone between the pair of side edge portions 22, 22 and the front and rear end portions 23, 24 bonded to the chassis 2 by means of a hot melt adhesive 26. The inner surface 34 of the body fluid absorbent structure 3 has at least a part thereof in the back-and-forth direction Y covered with at least one crossover member 31 extending across the body fluid absorbent structure 3 in the width direction X and having a width measured in the back-and-forth direction Y in a range of 5 to 250 mm. In the case of the embodiment shown in FIG. 2, the crossover member 31 comprises a pair of crossover sub-members 31a, 31b, of which the front crossover sub-member 31a is placed aside toward the front waist region 6 and the rear crossover sub-member 31b is placed aside toward the rear waist region 7. The crossover member 31 is formed from a belt-like sheet 32 extending across the body fluid absorbent structure 3. Referring to FIG. 3, transversely opposite side edge portions 33a of the crossover member 31 are bonded to the outer surface 35 of the body fluid absorbent structure 3 along the side edge portions 22 of the latter by means of adhesives 27 and an intermediate portion 33b between the side edge portions 33a is not bonded to, i.e., let free from the cover sheet 25 defining the inner surface 34 of the body fluid absorbent structure 3. An intermediate portion 33b of the crossover member 31 defined between the side edge portions 22 of the body fluid absorbent structure 3 preferably has a width larger than the width of the body fluid absorbent structure 3 so that the intermediate portion 33b is spaced apart upward from the cover member 25 of the body fluid absorbent structure 3 in a thickness direction of the absorbent panel 21. In the case of the crossover member 31 comprising a plurality of crossover sub-members as illustrated by FIG. 2, two crossover sub-members located in the vicinity of the wearer's anus and being adjacent to each other in the back-and-forth direction Y are preferably spaced apart from each other in the back-and-forth direction Y by a sufficient dimension w to form a clearance 30 through which feces discharged from the wearer can smoothly pass. The dimension W is preferably in a range of 10 to 150 mm. The crossover member 31 preferably has a bending resistance in a range of 10 to 150 with respect to a flexural deformation of the diaper 1 in the width direction. The bending resistance is measured using a method and apparatus prescribed by JIS (Japanese Industrial Standards) L 1913, Section 6.7.2. For measurement of the bending resistance, a sample having a width of 25 mm and a length of 150 mm may be obtained directly from the diaper 1 or from the same material as the crossover member 31 of the diaper 1.

The chassis 2 carrying the body fluid absorbent structure 3 attached thereto is provided in the vicinity of the respective side edges 22 of the body fluid absorbent structure 3 with leak-barrier cuffs 36. Each of these leak-barrier cuffs 36 is formed from a sheet extending in the back-and-forth direction Y, preferably from a liquid-impervious sheet. The leak-barrier cuff 36 is bonded to the chassis 2 along a proximal edge portion 37 and longitudinally opposite end portions 38, 39 using a suitable adhesive or welding technique wherein these longitudinally opposite end portions 38, 39 are covered with portions of the outer sheet 5 folded back onto the inner side of the diaper 1. The leak-barrier cuff 36 has its free side edge portion 41 is placed aside from the proximal end portion 37 inwardly of the diaper 1 and not bonded to, i.e., let free from the chassis 2, the body fluid absorbent structure 3 and the crossover member 31 in the crotch zone 8 as well as in the vicinity thereof. The sheet is folded back along the free side edge portion 41 to form a sleeve 42 and an elastic member 43 is bonded to the inner surface of this sleeve 42 while the elastic member 43 is stretched in the back-and-forth direction. As will be apparent to those skilled in the art, such leak-barrier cuffs 36 form pockets 44 adapted to open inwardly of the diaper 1.

Figure 4:
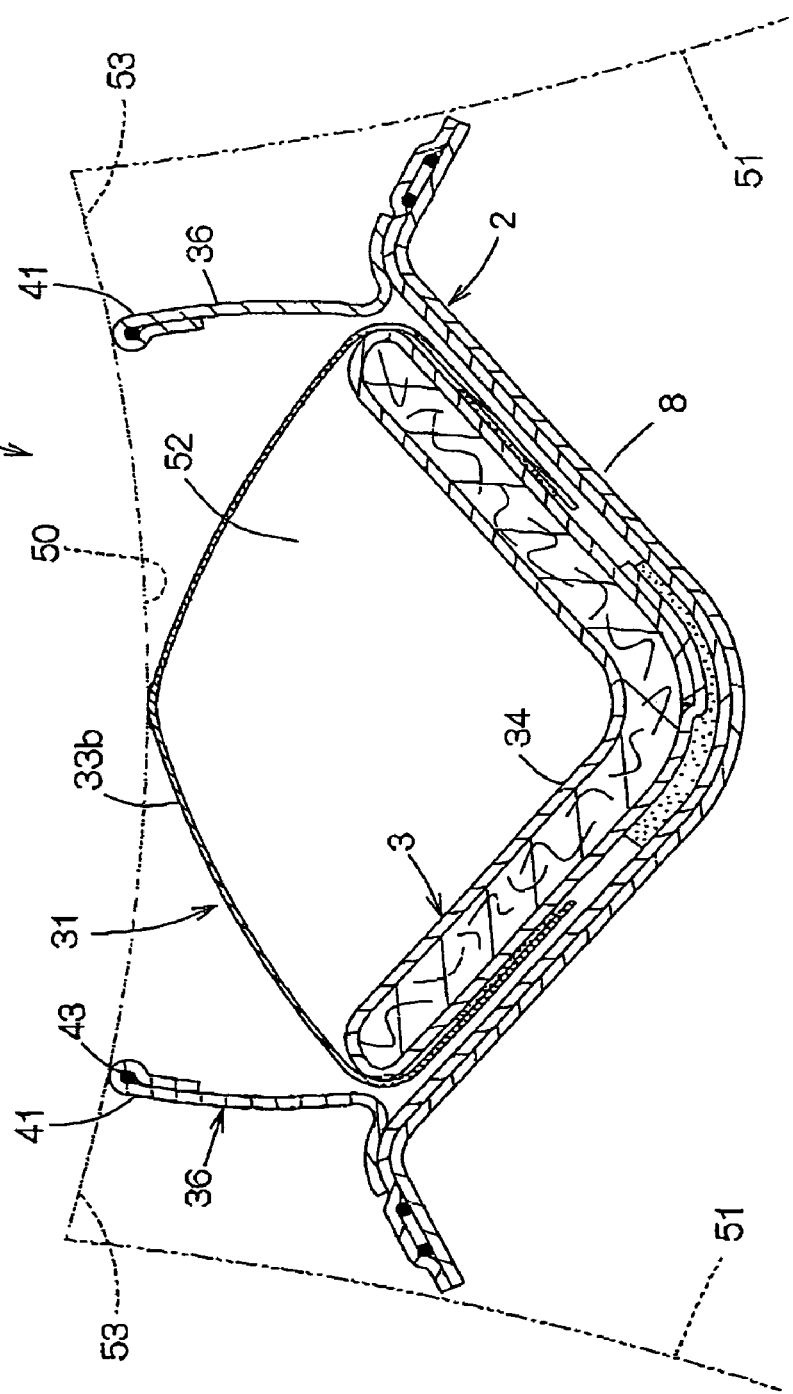
FIG. 4 is a view similar to FIG. 3, showing the crotch region being deformed.

FIG. 4 is a view similar to FIG. 3, showing the crotch region 8 deformed as the diaper 1 I put on the wearer's body. The crotch region 8 received between the wearer's thighs 51 as indicated by imaginary lines is deformed generally in a V-shape so that the chassis 2 and the body fluid absorbent structure 3 may become convex downward while the crossover member 31 may be deformed generally in an inverted V-shape or in a circular arc being convex upward. Consequently, the body fluid absorbent structure 3 and the crossover member 31 are adequately spaced apart from each other to form a tunnel-like space 52 extending in the back-and-forth direction of the diaper 1. Being deformed in this manner, the intermediate portion 33b of the crossover member 31 is elastically brought in loose contact with the wearer's crotch region 50 from below without uncomfortably irritating the wearer's skin. As the diaper 1 is curved in the back-and-forth direction to describe a U-shape in the course of transformation from the developed planar shape as shown in FIG. 2 to the pull-on type diaper 1, the leak-barrier cuffs 36 rise up above the inner surface of the chassis 2 due to contraction of the elastic members 43 and the free side edge portions 41 are brought in contact with the wearer's skin in the vicinity of the wearer's inguinal region 53 as seen in FIG. 4.

Feces discharged on the diaper in the state as illustrated in FIG. 4 passes the clearance 30 defined between the front crossover sub-member 31a and the rear crossover sub-member 31b and reaches the inner surface 34 of the body fluid absorbent structure 3. If feces is relatively fluid feces such as loose passage, such fluid feces will flow along the inner side of the tunnel-shaped space 52 and spread in the back-and-forth direction of the body fluid absorbent structure 3. However, it is unlikely that the fluid feces spreading in this manner might come in contact with the wearer's skin because such fluid feces can be reliably covered with the front crossover sub-member 31a and/or the rear crossover sub-member 31b. The crossover member 31 functioning in this manner preferably has a bending resistance in a range of 10 to 150 in order to ensure that the crossover member 31 may be appropriately deformed so as to become convex upward as seen in FIG. 4 and to come in loose contact with the wearer's skin without uncomfortably irritating the wearer's skin. With the bending resistance less than 10, the crossover member 31 will become excessively flexible and it will be difficult for the crossover member 31 to be deformed upward as expected. With the bending resistance exceeding 150, on the contrary, it will be difficult of the crossover member 31 to be flexibly deformed as the crossover member 31 comes in contact with the wearer's skin and uncomfortable irritation may occur.

The belt-like sheet 32 forming such crossover member 31 may be formed from a sheet material selected from the group consisting of a nonwoven fabric, woven fabric, plastic film, perforated plastic film and netty sheet. While the belt-like sheet 32 may be formed either from an elastically deformable sheet material or by an inelastically deformable sheet material, the elastically deformable sheet material facilitates the crossover member 31 to be deformed so as to become convex upward. Such elastically deformable sheet material may be selected from the group consisting of a nonwoven fabric made of crimped fibers such as crimped conjugate fibers, film and net made of elastomer such as natural or synthetic rubber, and formed plastic sheet made of urethane, polyethylene or polystyrene. It is also possible to use a hydrophobic sheet material or hydrophilic sheet material as a stock material for the belt-like sheet 32. The hydrophobic belt-like sheet 32 will be advantageous in that such crossover member 31 can maintain a dry touch even after urine has been discharged but disadvantageous in that urine is apt to flow sideways on the upper surface of the crossover member 31. On the contrary, the hydrophilic crossover member 31 will be advantageously able to prevent urine from flowing sideways on the upper surface of the crossover member 31 but may give the wearer uncomfortable wet feeling after urine has been discharged. In view of this, the hydrophobic fibers and hydrophilic fibers may be mixed with each other at an appropriate ratio to obtain the belt-like crossover r 31 having a hydrophobic property appropriately adjusted.

The inner sheet 4 of the chassis 2 may be formed from a nonwoven fabric or plastic film. The outer sheet 5 also may be formed from a nonwoven fabric or plastic film. Both the inner sheet 4 and the outer sheet 5 are preferably breathable and preferably at least one of these inner and outer sheets 4, 5 is liquid-impervious in order to prevent any amount of body fluids from back flowing and leaking from the diaper 1. While the outer sheet 5 is folded back onto the inner side of the chassis 2 along the front and rear end portions 2a, 2b in the embodiment shown in FIG. 1, it is not essential for the present invention to fold the outer sheet 5 in this manner.

In the body fluid absorbent structure 3, the core 21 may be formed from fluff pulp, a mixture of fluff pulp and super-absorbent polymer particles or super-absorbent polymer fibers, in any cases, compressed to obtain a panel of a desired shape and, if desired, such panel may be wrapped with a liquid-diffusible sheet such as a tissue paper. Alternatively, it is possible to use a water-absorbent panel obtained by laminating a plurality of body fluid absorbent sheet material such as a rayon paper, tissue paper or woven fabric made of natural fibers as the absorbent absorbent structure 21. The cover sheet 25 for the absorbent panel 21 may be selected from the group including a liquid-absorbent nonwoven fabric, liquid-absorbent perforated plastic film and tissue paper. Alternatively, it is possible to cover the outer surface 21b of the absorbent panel 21 facing the chassis 2 with a liquid-impervious sheet and to cover the inner surface 21a of the absorbent panel 21 facing the wearer's skin with a liquid-pervious sheet. The leak-barrier cuffs 36 may be formed from a sheet material such as a nonwoven fabric or plastic film. Such sheet material is preferably liquid-impervious and more preferably breathable liquid-impervious.

Figure 5:
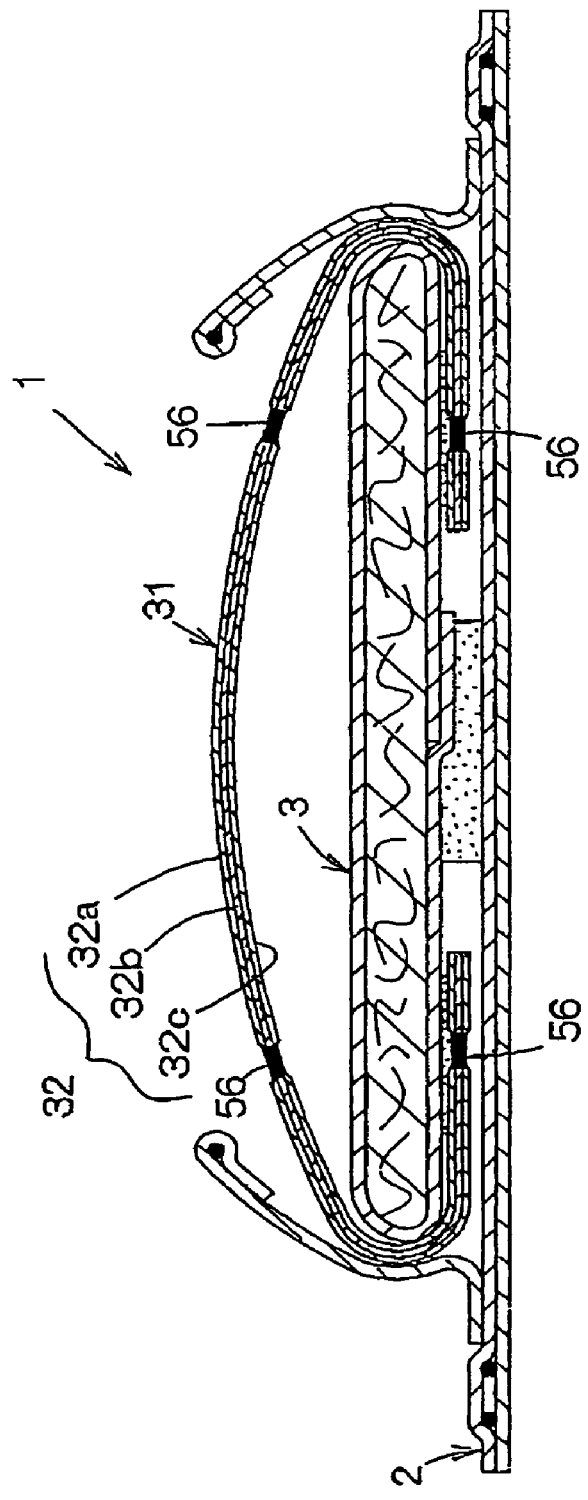
FIG. 5 is a view similar to FIG. 3, showing the other preferred embodiment of the invention.

FIG. 5 is a view similar to FIG. 3, showing one preferred embodiment of the invention. In this diaper 1, the crossover member 31 is formed from a belt-like sheet 32 comprising three sheets 32a, 32b, 32c which are identical in shape as well as in size and laminated one on another. Three sheets 32a, 32b, 32c are partially bonded together at appropriately distributed spots 56 using an adhesive or welding technique. The respective sheets 32a, 32b, 32c may be formed from a flexible nonwoven fabric to ensure a soft touch while they may be partially bonded together to ensure a desired bending resistance. In this way, the crossover member 31 adapted to be smoothly deformed to become convex upward can be provided without sacrificing a desired touch. It is also possible to obtain the desired belt-like sheet 32 using a nonwoven fabric having a bending resistance sufficiently low to ensure a soft touch as the sheet material 32a forming the uppermost layer and using sheet materials having a relatively high bending resistance as the sheet materials 32b, 32c forming the intermediate and lowermost layers.

Figure 6:
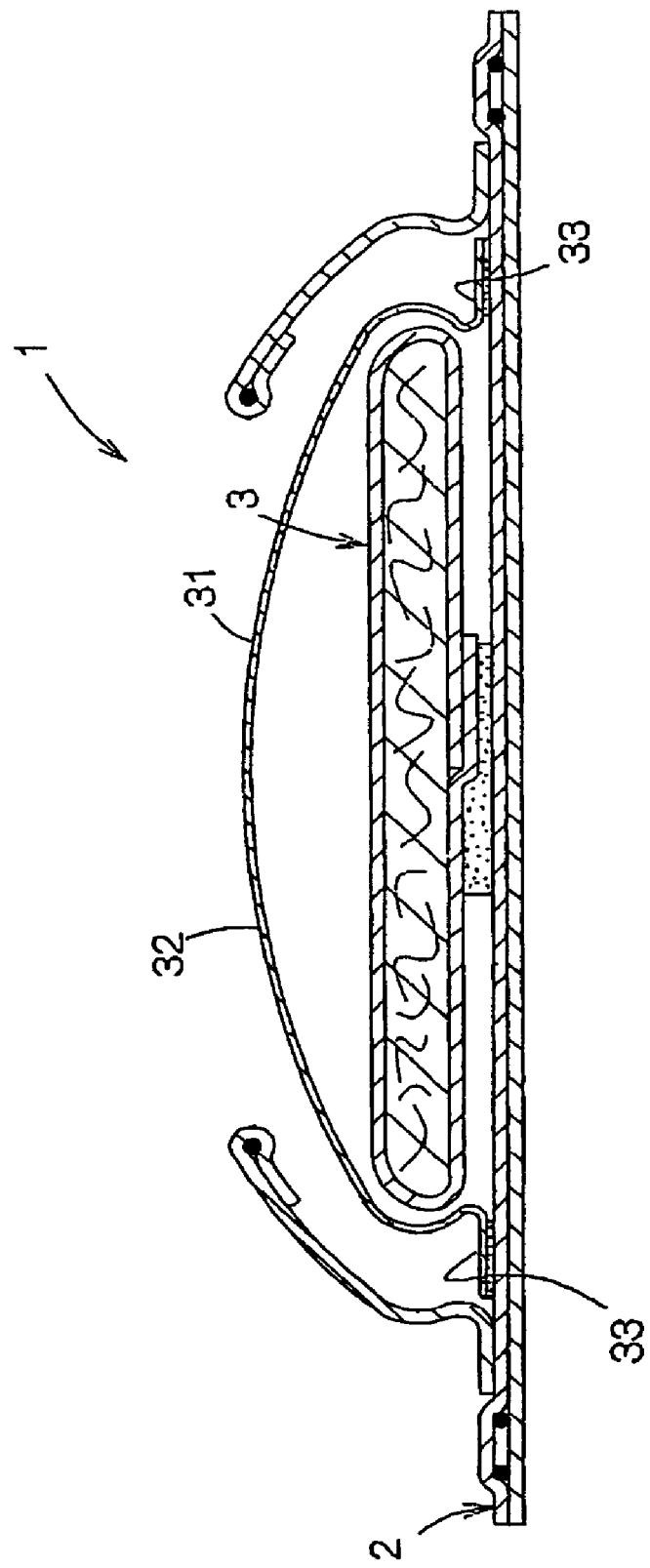
FIG. 6 is a view similar to FIG. 3, showing another preferred embodiment of the invention.

FIG. 6 also is a view similar to FIG. 3, showing another preferred embodiment of the invention. In this diaper 1, the transversely opposite end portions 33a of the crossover member 31 are folded outward in the width direction of the diaper 1 so that the crossover member 31 presents an Ω-shaped cross-section. Depending on physical properties of the belt-like sheet 32, such shape of cross-section facilitates the crossover member 31 to be sufficiently spaced from the body fluid absorbent structure 3 as the crossover member 31 is curved so as to become convex upward.

Figure 7:
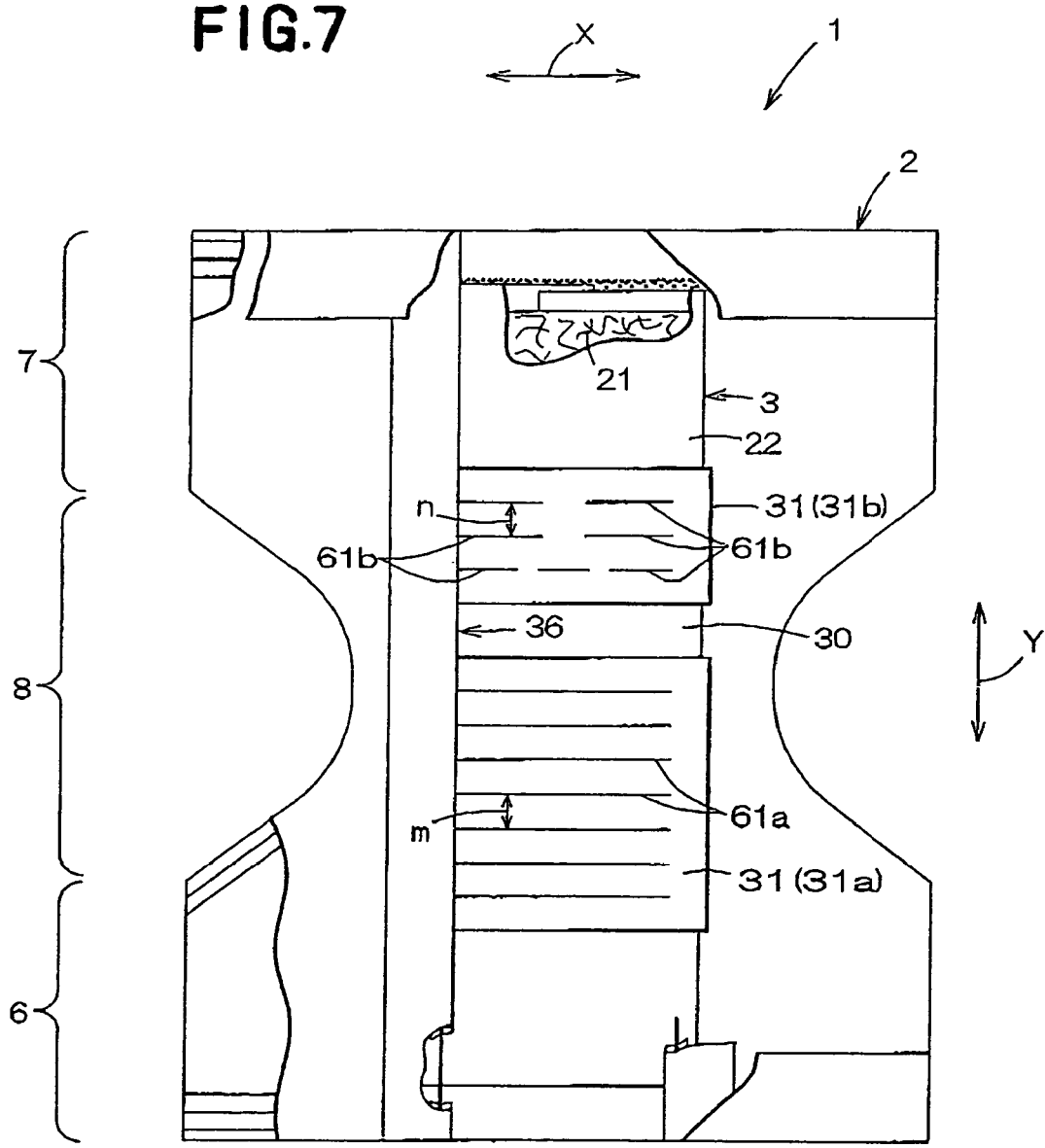
FIG. 7 is a view similar to FIG. 2, showing still another preferred embodiment of the invention.

FIG. 7 also is a view similar to FIG. 2, showing still another preferred embodiment of the invention. In this diaper 1, the crossover member 31 comprises the front crossover sub-member 31a and the rear crossover sub-member 31b respectively formed with first and second slits 61a, 61b extending in the width direction X of the diaper 1, preferably extending across the body fluid absorbent structure 3. A dimension m between each pair of the adjacent first slits 61a as well as a dimension n between each pair of the adjacent second slits 61b is preferably in a range of 2 to 80 mm. Just above the body fluid absorbent structure 3, both the front crossover member 31a and the rear crossover member 31b are respectively divided by the first and second slits 61a, 61b in a plurality of sections. These slits 61a, 61b facilitate the crossover member 31 to come in close contact with the wearer's skin having a irregular contour as the diaper 1 is put on the wearer's body. Urine and/or loose passage can flow through these slits 61a, 61b into the space defined between these crossover member 31 and the body fluid absorbent panel 3 and there is no anxiety that such urine and/or loose passage might wet again the wearer's skin. With the diaper 1 having the first slits 61a in the front crossover sub-member 31a and/or the second slits 61b in the rear crossover sub-member 31b, even when the clearance 30 is not properly aligned with the anus, body waste can reach the body fluid absorbent panel 3 through those first and second slits 61a, 61b. While the first slits 61a are continuously formed in the width direction x and the second slits 61b are intermittently formed in the width direction X in the embodiment illustrated in FIG. 7, the first slits 61a may be intermittently formed and the second slits 61b may be continuously formed to exploit the present invention.

Figure 8:
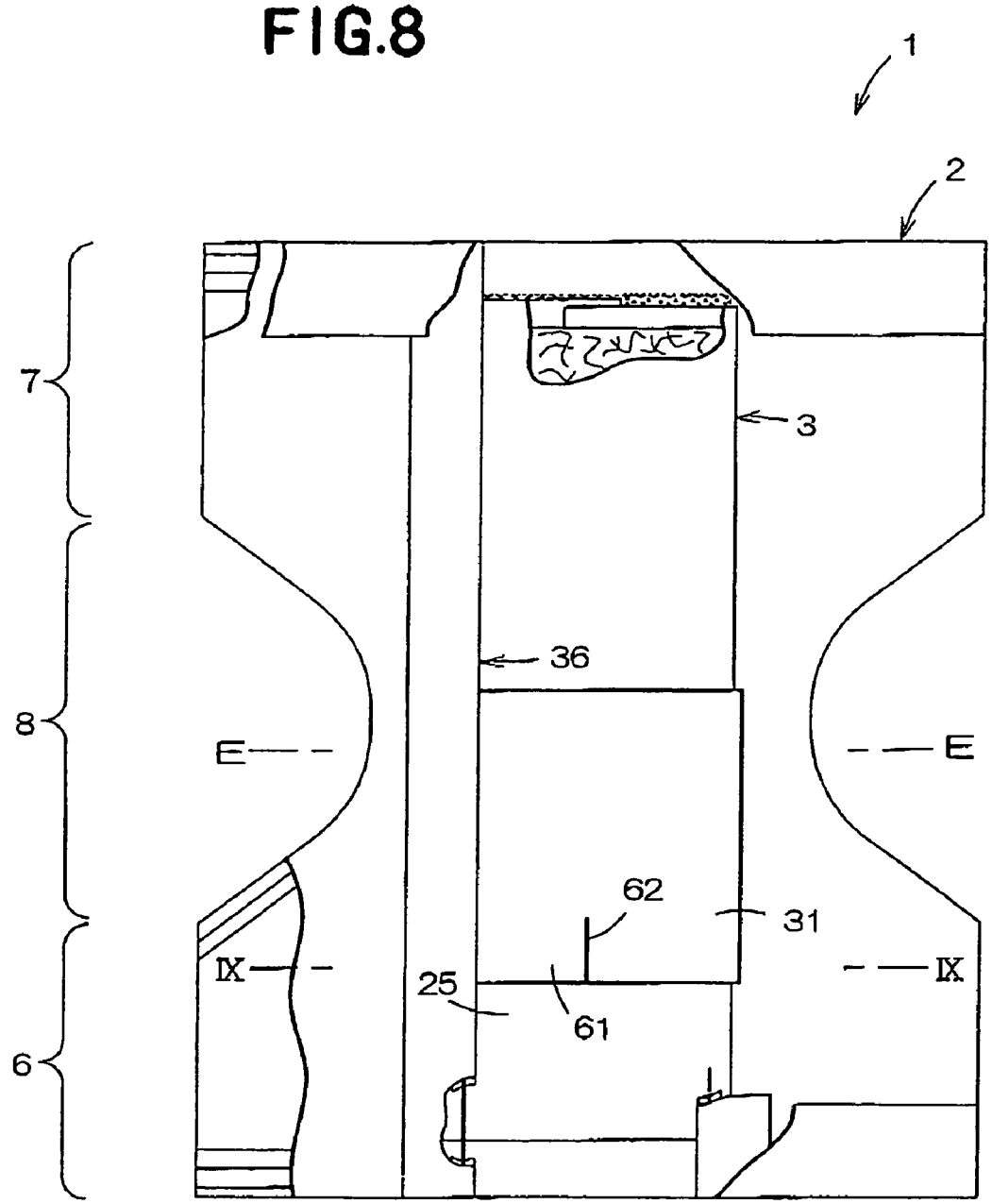
FIG. 8 is a view similar to FIG. 2, showing further another preferred embodiment of the invention.

FIG. 8 also is a view similar to FIG. 2, showing further another preferred embodiment of the invention. This diaper 1 is provided the single crossover member 31 placed aside toward the front waist region 6. This crossover member 31 is substantially the same as the front crossover sub-member 31a in the embodiment illustrated by FIG. 3 with respect to the position as well as to the dimension except that this crossover member 31 is provided in the vicinity of its front end with a bonding region 62 in which the crossover member 31 is bonded to the cover sheet 25 using an adhesive or welding technique. A cross-sectional shape of this diaper 1 along a line E-E in the crotch region 8 is substantially the same as that seen in FIG. 3, so a repeated description on, this cross-sectional shape is eliminated here. Depending on the size of the individual diaper, a width of the crossover member 31 may be adjusted in a range of 5 to 250 mm. While the crossover member 31 is preferably placed aside toward the front waist region 6 as will be seen in FIG. 8, such position may be appropriately adjusted in the back-and-forth direction Y. It is possible to provide this diaper 1 also with slits similar to the first slits 61a or the second slits 61b in the embodiment illustrated in FIG. 7.

FIG. 9 is a sectional view taken along the line IX-IX in FIG. 8. Referring to FIG. 8, the line IX-IX extends across the bonding region 62. The bonding region 62 in which the crossover member 31 is bonded to the cover sheet 25 in a transversely middle zone of the diaper 1 serves to limit a dimension by which the crossover ember 31 is spaced apart toward the waist-hole 11 (See FIG. 1) from the cover sheet 25. Such pull-on diaper 1 is convenient particular when the diaper 1 is put on an infant because there is no anxiety that the infant's tiptoe might be unintentionally guided into the space defined between the crossover member 31 and the cover sheet 25.

FIG. 10 also is a view similar to FIG. 3, showing further additional preferred embodiment of the invention. In this diaper 1, the inner sheet 4 of the pull-on type chassis 2 is formed from a liquid-pervious nonwoven fabric and the outer sheet 5 of the chassis 2 is formed from a liquid-impervious plastic film. The body fluid absorbent structure 3 comprises the body fluid absorbent panel 21 and the inner sheet 4 covering the surface of the panel 21 facing the wearer's skin. The absorbent panel 21 is formed by a batt comprising a mixture of fluff pulp and super-absorbent polymer particles or a batt comprising these components laminated together and wrapped with a tissue paper. Such batt is interposed between the inner and outer sheets 4, 5 and bonded to the inner surface of at least one of these sheets 4, 5 by means of a hot melt adhesive (not shown). The belt-like sheet 32 forming the crossover member 31 is formed from a nonwoven fabric made of thermoplastic synthetic fibers and has its transversely opposite end portions 33a folded inward and bonded to the inner sheet 4 at positions spaced outward from the transversely opposite side edge portions 22 of the absorbent panel 21 using an adhesive or welding technique. The inner sheet 4 is utilized in this manner to constitute the chassis 2 and simultaneously to constitute the body fluid absorbent structure 3 with such diaper 1 also, a sufficient space is formed below the crossover member 31 as the diaper 1 is put on the wearer's body just as the embodiment illustrated in FIG. 3 is the case.

If the crossover member 31 contains suitable thermoplastic synthetic resin to ensure that the transversely opposite end portions 33a of the crossover member 31 are reliably directed inward or outward of the diaper 1 and the intermediate portion 33b reliably become convex upward, the crossover member 31 can be previously thermoformed so that the cross-section may present a C- or an Ω-shape. While the invention has been described above on the basis of the pull-on type diaper 1 as a specific embodiment, the invention is applicable also to the open type diaper.

The disposable diaper according to the present invention is provided with a plurality of the crossover members each describing a circular arc above the body fluid absorbent structure so that urine and/or feces passing through the clearance defined between each pair of the adjacent crossover members into the space defined between these crossover members and the body fluid absorbent structure may be prevented by the presence of these crossover members from coming in contact with the wearer's skin. The crossover members have an appropriate bending resistance such that the crossover members may be elastically brought in loose contact with the wearer's skin as these crossover members are deformed so as to describe circular arcs being convex upward. Therefore, it is unlikely that the crossover members might locally irritate the wearer's skin and/or cause a rash of the wearer's skin. The crossover members formed with the slits allow urine and/or loose passage to reach the body fluid absorbent panel through these slits.

What is claimed is:

1. A disposable diaper, comprising:
a chassis;
at least one crossover member; and
a body fluid absorbent structure having opposite inner and outer surfaces;
said chassis having
a back-and-forth direction, and a width direction orthogonal to the back-and-forth direction,
a front waist region, a rear waist region and a crotch region extending in the back-and-forth direction between the front and rear waist regions, and
an inner surface adapted to face a wearer's skin, in use, and an outer surface adapted to face away from the wearer's skin, in use;
said absorbent structure comprising
a body fluid absorbent panel lying on said inner surface of said chassis so as to extend in at least said crotch region, and
a liquid-pervious sheet covering a surface of said absorbent panel adapted to face the wearer's skin, in use, and defining at least said inner surface of said absorbent structure;
said absorbent structure being dimensioned in said crotch region to be narrower than said crotch region and having a pair of side edge portions extending in said back-and-forth direction and front and rear end portions extending in said width direction;
on the side adapted to face said wearer's skin, in use, said liquid-pervious sheet being opposed to said at least one crossover member that extends across said absorbent structure above said absorbent structure in said width direction and has a length in a range of 5 to 250 mm as measured in said back-and-forth direction; and
said crossover member comprising, in the width direction,
transversely opposite end portions bonded to said diaper in a vicinity of and along said side edge portions of said absorbent structure, and
an intermediate portion defined between said transversely opposite end portions and free of direct bonding to the diaper, said intermediate portion being deformable so as to become convex from said outer surface toward said inner surface as said chassis and said absorbent structure are deformed in said crotch region so as to become convex from said inner surface toward said outer surface and to reduce respective widths of said chassis and absorbent structure;
wherein
said crossover member is free of absorbent material;
said diaper comprises a pair of said crossover members being adjacent to each other in said back-and-forth direction, located in a vicinity of an area adapted to correspond to the wearer's anus, in use, and entirely spaced apart from each other in said back-and-forth direction by a spacing in a range of 10 to 150 mm to define a passage for excrement discharged by the wearer to pass through the spacing defined between said adjacent crossover members;
said diaper further comprises a pair of leak-barrier cuffs located, in the width direction, outboard of and extending, in the back-and-forth direction, along the side edge portions of said absorbent structure;
said crossover member is free of direct attachment to the leak-barrier cuffs; and
said outer surface of said absorbent structure has, between said side edge portions and between said front and rear end portions, an intermediate zone directly bonded to the inner surface of said chassis, whereas the side edge portions on opposite sides of said intermediate zone are free of direct attachment to said chassis.

2. The disposable diaper as set forth by claim 1, wherein said leak-barrier cuffs are elastically stretchable and contractible in said back-and-forth direction and each said crossover member is entirely located, in the width direction, between said leak-barrier cuffs.

3. The disposable diaper as set forth by claim 1, wherein the end portions of said crossover member are directly bonded to the absorbent structure and the crossover member is entirely free of direct attachment to the chassis.

4. A disposable diaper, comprising:
a chassis;
at least one crossover member; and
a body fluid absorbent structure having opposite inner and outer surfaces;
said chassis having
a longitudinal direction, and a transverse direction orthogonal to the longitudinal direction,
a front waist region, a rear waist region and a crotch region extending in the longitudinal direction between the front and rear waist regions, and
an inner surface adapted to face a wearer's skin, in use, and an outer surface adapted to face away from the wearer's skin, in use;
said absorbent structure comprising
a pair of side edge portions extending in said longitudinal direction and front and rear end portions extending in said transverse direction,
a body fluid absorbent panel lying on said inner surface of said chassis so as to extend in at least said crotch region, and
a liquid-pervious sheet covering a surface of said absorbent panel adapted to face the wearer's skin, in use, and defining at least said inner surface of said absorbent structure;
said crossover member different from said liquid-pervious sheet and comprising, in the transverse direction,
transversely opposite end portions directly bonded to one of said absorbent structure and said chassis in a vicinity of and along said side edge portions of said absorbent structure, and
an intermediate portion defined between and connecting said transversely opposite end portions, and being free of direct attachment to both said chassis and absorbent structure, said intermediate portion being deformable and convex away from said chassis and said absorbent structure;
wherein
an entirety of said crossover member is free of absorbent material and the intermediate portion of said crossover member is free of direct attachment to any absorbent material;
said diaper further comprises a pair of leak-barrier cuffs located, in the transverse direction, outboard of and extending, in the longitudinal direction, along the side edge portions of said absorbent structure;

the intermediate portion of said crossover member is free of direct attachment to the leak-barrier cuffs;

said crossover member has longitudinally opposite front and rear ends extending in the transverse direction across the absorbent structure and being free of direct attachment to said chassis and said absorbent structure;

said crossover member defines together with said absorbent structure a channel having, in the longitudinal direction, two open ends at said front and rear ends of said crossover member, respectively;

said crossover member is entirely located, in the transverse direction, between the leak-barrier cuffs;

said outer surface of said absorbent structure has, between said side edge portions and between said front and rear end portions, an intermediate zone directly bonded to the inner surface of said chassis, whereas said outer surface of said absorbent structure in the side edge portions on opposite sides of said intermediate zone is free of direct attachment to said chassis; and wherein said diaper comprises a pair of said crossover members being adjacent to each other in said longitudinal direction, located in a vicinity of an area adapted to correspond to the wearer's anus, in use, and entirely spaced apart from each other in said longitudinal direction by a spacing in a range of 10 to 150 mm to define a passage for excrement discharged by the wearer to pass through the spacing between said adjacent crossover members;

each said crossover member comprising a plurality of slits elongated in said transverse direction between the transversely opposite end portions of said crossover member;

each of said slits extending through an entire thickness of the respective crossover member to allow body waste to pass though the crossover member though the slits to reach the absorbent structure; and a pattern in which the slits of one of the crossover members are arranged is different from that of the slits of the other crossover member.

* * * * *